(12) United States Patent
Tselepis et al.

(10) Patent No.: US 9,421,220 B2
(45) Date of Patent: Aug. 23, 2016

(54) ANTI-CANCER COMPOSITION COMPRISING ALGINATE

(75) Inventors: Chris Tselepis, Birmingham (GB); Tariq Iqbal, Birmingham (GB); Owen James Sansom, Glasgow (GB)

(73) Assignee: THE UNIVERSITY OF BIRMINGHAM EDGBASTON, Birmingham (GB)

(*) Notice: Subject to any disclaimer, the term of this patent is extended or adjusted under 35 U.S.C. 154(b) by 0 days.

(21) Appl. No.: 13/503,978

(22) PCT Filed: Oct. 26, 2010

(86) PCT No.: PCT/GB2010/001987
§ 371 (c)(1),
(2), (4) Date: Jul. 16, 2012

(87) PCT Pub. No.: WO2011/051665
PCT Pub. Date: May 5, 2011

(65) Prior Publication Data
US 2012/0276163 A1    Nov. 1, 2012

(30) Foreign Application Priority Data

Oct. 26, 2009 (GB) .................................. 0918722.0

(51) Int. Cl.
*A61K 31/734* (2006.01)
*A61K 9/20* (2006.01)
*A61K 9/28* (2006.01)

(52) U.S. Cl.
CPC ............. *A61K 31/734* (2013.01); *A61K 9/205* (2013.01); *A61K 9/2054* (2013.01); *A61K 9/286* (2013.01)

(58) Field of Classification Search
USPC .................................. 424/400; 514/54; 536/3
See application file for complete search history.

(56) References Cited

U.S. PATENT DOCUMENTS

| 5,602,180 A * | 2/1997 | Bennett .......................... 514/578 |
| 7,229,818 B2 * | 6/2007 | Porubcan ...................... 435/260 |
| 2009/0074944 A1 * | 3/2009 | Xie et al. ..................... 427/2.14 |

FOREIGN PATENT DOCUMENTS

| EP | 0 055 618 A1 | 7/1982 |
| JP | 10-324642 | 8/1998 |
| TW | 546287 B | 8/2003 |
| WO | WO 2009/027955 A2 | 3/2009 |
| WO | WO 2009/053628 A2 | 4/2009 |
| WO | WO 2009/107322 A1 | 9/2009 |

OTHER PUBLICATIONS

Alvarez-Fuentes et al., J. Drug Targeting, Oct.-Dec. 2004, vol. 12(9-10), pp. 607-612.*

English Translation of Chinese Second Office Action, dated Dec. 12, 2013, issued in Chinese Patent Application No. 2009801326369 (13 pgs).

Siegers, C.P., et al; "Influence of dietary iron overload on cell proliferation and intestinal tumorigenesis in mice"; *Cancer Lett*; vol. 65, No. 3, pp. 245-249 (1992) PubMed Abstract.

Text of Second Office Action issued in Chinese PCT National Phase Patent Application No. 201080059192.3, Based on PCT/GB2010/001987, filed Oct. 26, 2010 (4 pgs).

Siegers, C.P., et al; "Influence of dietary iron overload on cell proliferation and intestinal tumorigenesis in mice"; *Cancer Lett*; vol. 65, No. 3, pp. 245-249 (1992).

Siegers, C.-P., et al; "Dietary Iron Enhances the Tumor Rate in Dimethylhydrazine-Induced Colon Carcinogenesis in Mice", *Cancer Letters*, vol. 41, No. 3, pp. 251-256 (1998).

Hattori, Y., et al; "Novel irinotecan-loaded liposome using phytic acid with high therapeutic efficacy for colon tumors"; *Journal of Controlled Release*, vol. 136, No. 1, pp. 30-37 (2009) XP026103525.

Giftson, Jebakkan Senapathy, et al; "Chemopreventive efficacy of gallic acid, an antioxidant and anticarcinogenic polyphenol, against 1,2-dimethyl hydrazine induced rat colon carcinogenesis"; *Investigational New Drugs; The Journal of New Anticancer Agents*; vol. 28, No. 3, pp. 251-259 (2009) XP19788464.

Pan, L., et al; "Natural cloudy apple juice and polyphenol-enriched apple juice extract prevent intestinal adenoma formation in the APCMin/+model for colon cancer prevention"; *European Journal of Cancer, Supplement*, vol. 4, No. 1, pp. 55-56 (2006) XP024989204.

Patel, et al; "Polymeric black tea polyphenols inhibit 1,2-dimethylhylhydrazine induced colorectal carcinogenesis by inhibiting cell proliferation via Wnt/beta-catenin pathway"; *Toxicology and Applied Pharmacology*, vol. 227, No. 1, pp. 136-146 (2007) XP022452997.

Japanese Patent Application No. 2012-535916, dated Jul. 2, 2015; Office Action, Final Notification of Reasons for Refusal dated Jul. 7, 2015 (4 pgs).

Japanese Patent Application No. 2012-535916, dated Jul. 2, 2015; Office Action, Final Notification of Reasons for Refusal dated Jul. 7, 2015, English Translation (9 pgs).

Jebakkan, Senapathy Giftson, et al; "Chemopreventive efficacy of gallic acid, an antioxidant and anticarcinogenic polyphenol, against 1,2-dimethyl hydrazine induced rat colon carcinogenesis"; *Investigational New Drugs; The Journal of New Anticancer Agents*; vol. 28, No. 3, pp. 251-259 (2009) XP19788464.

Patel, et al; "Polymeric black tea polyphenols inhibit 1,2-dimethylhylhydrazine induced colorectal carcinogenesis by in hibiting cell proliferation via Wnt/beta-catenin pathway"; *Toxicology and Applied Pharmacology*, vol. 227, No. 1, pp. 136/146 (2007) XP022452997.

* cited by examiner

*Primary Examiner* — Michael G Hartley
*Assistant Examiner* — Robert Cabral
(74) *Attorney, Agent, or Firm* — Nixon & Vanderhye P.C.

(57) ABSTRACT

Biologically acceptable composition for the prophylaxis and/or treatment of colorectal cancer. The composition contains an iron chelator, and the composition is adapted for the selective targeting of the iron chelator to the colon. The iron chelator is non-digestible, non-absorbable and non-fermentable in the gastrointestinal tract.

3 Claims, No Drawings

ANTI-CANCER COMPOSITION COMPRISING ALGINATE

This application is the U.S. national phase of International Application No. PCT/GB2010/001987 filed 26 Oct. 2010 which designated the U.S. and claims priority to British Application No. 0918722.0 filed 26 Oct. 2009, the entire contents of each of which are hereby incorporated by reference.

The present invention relates to a composition for human or animal consumption. In particular, the present invention relates to a composition for prevention and/or treatment of colorectal cancer.

Colorectal cancer is one of the major causes of cancer death in Western Societies. In the UK, the disease is the second commonest cause of cancer mortality. Approximately 37,000 cases are diagnosed each year, and around 16,000 deaths per year are caused by the disease.

A large number of factors are linked to an increased risk of developing colorectal cancer. These include age, a genetic predisposition, a family history of colorectal cancer, a personal history of inflammatory bowel disease, and lifestyle-related factors. Lifestyle-related factors such as obesity, smoking, high alcohol intake, diet and a lack of exercise have all been linked to colorectal cancer.

In particular, the high prevalence of this type of cancer in Western cultures has been linked to the Western diet which is high in processed and red meat. It is not exactly understood which components present in these types of foods contribute to the increased cancer risk. It has previously been suggested that the cooking and processing of meats at high temperatures creates carcinogenic chemicals. The high levels of fat in meat have also been hypothesised to contribute to the development of cancer.

Another hypothesis is that high levels of iron (Fe), such as those found in red meat, may be linked to colorectal cancer, although previous in vitro studies and animal models investigating the effects of iron on colorectal cancer have produced mixed results, and it has remained unclear how iron mediates carcinogenesis.

Given the prevalence of the disease in today's society, it is clear that furthering our understanding of the causes of colorectal cancer and finding new ways to prevent, manage or even cure the disease is of extreme importance.

With this in mind, the object of the present invention is to aid the prevention of colorectal cancer and/or aid the management or treatment of colorectal cancer in patients who already have the disease.

According to a first aspect of the present invention there is provided a biologically acceptable composition for the prophylaxis and/or treatment of colorectal cancer comprising an iron chelator, wherein said composition is adapted for the selective targeting of the iron chelator to the colon.

According to a second aspect of the present invention there is provided an orally deliverable pharmaceutical composition comprising an iron chelator, wherein the iron chelator is unable to bind iron until the composition reaches the colon.

In a third aspect, the present invention resides in the use of an iron chelator for the treatment of a mammal afflicted with colorectal cancer or prophylaxis in a mammal at risk of colorectal cancer, by selective administration of a therapeutically effective amount of said iron chelator to the colon.

According to a fourth aspect of the present invention there is provided a method of treating a mammal afflicted with colorectal cancer or preventing colorectal cancer in a mammal at risk of colorectal cancer comprising selective administration of a therapeutically effective amount of an iron chelator to the colon.

In some embodiments the mammal is human.

It will be understood that a chelator binds free metal ions and removes them from solution. Metal ions bound by a chelator molecule are effectively inactivated because they are no longer available to react with other chemical species. Chelators are usually specific for particular metal ions. An iron chelator is a chelator that binds Fe ions. In certain embodiments said chelator may be iron specific.

By "selective targeting to the colon" and "selective administration", it will be understood that the composition has no iron-chelating effect until it reaches the colon. This may also be referred to as "colonic delivery".

Colonic delivery of the iron chelator may be achieved by oral or rectal administration of the composition.

For rectal administration, the composition may be in the form of a suppository incorporating the iron chelator and a carrier such as cocoa butter, or in the form of an enema.

For oral administration, the composition may be in the form of discrete units such as capsules, cachets, tablets or lozenges, each containing a predetermined amount of the iron chelator; in the form of a powder or granules; in the form of an emulsion, suspension in an aqueous liquid or non-aqueous liquid. The composition may also be in the form of a bolus, electuary or paste.

In some embodiments, the composition comprising the iron chelator is micro-encapsulated. Microcapsules may be conveniently administered in foods, drinks, smoothies and the like.

For oral administration, colonic delivery of the iron chelator may be achieved by ingestion of the iron chelator in an inactivated form, or in a form which otherwise prevents the iron chelator from binding iron until it reaches the colon. Alternatively, the iron chelator may be ingested in the form of a precursor or prodrug, which is activated or modified in vivo such that the active iron chelator is only released in the colon.

In some embodiments, the composition comprising the iron chelator is encapsulated by a coating which remains intact while the composition passes through the stomach and small intestine, but which degrades in the colon. In a series of embodiments, colonic delivery is achieved using a coating which is pH sensitive, time-dependent, pressure-dependent or degradable by colic bacteria. In a particular embodiment, the composition is encapsulated or micro-encapsulated to ensure that the iron chelator is not available before it reaches the colon. The composition may be encapsulated or micro-encapsulated by a biodegradable coating. The coating may be a polymer. In other embodiments, the coating involves colon-targeted microsponges, or a microbially-triggered osmotic pump. The composition may be targeted to the colon by a combination of the above strategies.

In embodiments, the coating is a biodegradable polysaccharide. The coating may comprise one or more biodegradable polysaccharides selected from the group consisting of albizia gum, alginates, amylose, arabinogalactan, cellulose, chitosan, chondroitin sulphate, curdlan, cyclodextrin, dextran, furcelleran, galactomannan, gellan gum, guar gum, hyaluronic acid, inulin, kara gum, karaya gum, locust bean gum, scleroglucan, starch, pectin, pulluvan or xylan.

The iron chelator may be naturally occurring, or it may be man-made (i.e. synthetic). In some embodiments, the chelator is naturally-occurring.

In some embodiments, the iron chelator is a hydrocolloid. In further embodiments, the iron chelator is a polysaccharide. The iron chelator may be selected from pectin, carrageenan, agarose sulphate, gellan, xanthan, agarose, guar, locust bean gum, phytic acid, tea flavonoids (catechins), melanoidins, curcumin, capsaicin, polyphenols or alginates, or it may be a combination of any of the above Advantageously, since some of these potential iron chelators are found in foods, it is known that they are safe for human consumption, and it is likely that they will impact on the levels of luminal iron when ingested.

In some embodiments, the iron chelator is non-digestible, non-absorbable and non-fermentable in the gastrointestinal tract. A chelator which is not digested or degraded by the body will be more effective at binding excess iron. If the chelator cannot be absorbed, any iron bound by the chelator will also be prevented from being absorbed by the body. The iron will therefore be removed from the body as an iron-chelator complex.

In some embodiments, the composition comprises alginate. In some particular embodiments, the composition comprises sodium alginate.

In addition to an iron chelator, the composition of the present invention may include one or more additional pharmaceutically acceptable ingredients such as excipients, bulking agents, diluents, buffers, flavouring agents, binders, surface active agents, sweeteners or flavourings, thickeners, lubricants and preservatives.

In some embodiments, the iron chelator is alginate.

In some embodiments, the amount of alginate administered is no more than 20 g, no more than 15 g, no more than 10 g or no more than 5 g per day. In some embodiments, the amount of alginate administered is no less than 1 g, no less than 2 g, no less than 5 g or no less than 10 g per day. In a series of embodiments, the amount of alginate administered is from 0.1 g to 4 g per day, from 0.2 g to 3 g per day, from 0.4 g to 2 g per day or from 0.5 g to 1.5 g per day, which may be administered as a single dose or as multiple doses (e.g. 2, 3 or 4 doses at intervals of e.g. 3, 6 or 8 hours).

There is a growing body of evidence implicating iron in carcinogenesis, and in particular colorectal cancer. Previous in vitro studies by the inventors compared the effect of iron on normal human colonic cells with the effect of iron on cells containing a mutant APC protein (A role for iron in Wnt signaling, Brookes M J, Boult J, Roberts K, Cooper B T, Hotchin N A, Matthews G, Iqbal T, Tselepis C. Oncogene. 2008 Feb. 7; 27(7):966-75). This mutation is associated with a predisposition to cancer development. From these experiments it was discovered that normal cells exposed to increased levels of iron showed no phenotypic effects. However, increased cellular viability and proliferation was observed in cells deficient in the APC protein as a result of exposure to iron. These results have led to the conclusion that excess iron may exacerbate tumorigenesis or increase the risk of cancer development in the background of APC loss, a common finding in cancers. However, until now it has remained unclear by what mechanism the iron was having an effect.

Through further extensive experimentation, the inventors have now discovered that it is the high level of iron present in the lumen of the colon, as opposed to the iron circulating in the blood, which poses the greatest cancer risk.

To delineate how iron mediates colorectal carcinogenesis in-vivo, further experiments were carried out using the 'Apc$^{Min/+}$' mouse. These mice carry a mutation which disrupts the ability of the APC tumour suppressor to bind and turnover b-catenin, and the mice develop 100's of benign adenomas. This model therefore represents an excellent model to test potential chemopreventive agents.

Apc$^{Min/+}$ mice were fed a standard control diet (n=17) or an iron deficient diet (n=11) immediately post weaning with tumour burden being assessed at 80 days of age. In addition mice were fed a high iron diet (standard control diet supplemented with 2% reduced pentacarbonyl iron (Harlan UK)) (n=6) but in these animals tumour burden was assessed at 45 (n=6) days of age. A fourth group of Apc$^{Min/+}$ mice (n=9), were fed the standard control diet but upon reaching 50 days of age were injected sub-cutaneously with iron dextran (50 mgs) with tumour burden being assessed at 85 days of age. A fifth group of Apc$^{Min/+}$ mice (n=9), were fed the standard control diet and post weaning were injected daily sub-cutaneously with the systemic iron chelator desferioxamine (200 mgs/kg). Feeding Apc$^{Min/+}$ mice an iron deficient diet resulted in a dramatic and statistical decrease in tumour number, size and overall tumour burden. To ensure that this was not attributed to a resulting systemic iron deficiency, mice were co-administered with iron dextran. The results of these experiments still showed a suppression of tumour burden despite systemic iron supplementation. Increasing and/or decreasing the systemic iron levels by iron dextran and desferioxamine respectively in Apc$^{Min/+}$ mice fed the control diet comparably showed no effect either on tumour number, size or tumour burden compared to control mice. Feeding Apc$^{Min/+}$ mice an iron loaded diet for two weeks alone resulted in a dramatic and statistical increase in tumour number. H&E staining of small bowel harvested at day 45 clearly showed the presence of adenomas in mice fed the iron loaded diet compared to mice on the control diet. This has most recently been supported in the Lgr5CreER+ Apc$^{fl/fl}$ model; another murine model of intestinal tumourigenesis. These studies have shown that a high iron diet accelerates intestinal tumourigenesis as exemplified by decreased survival in mice fed the iron rich diet compared to control diet. This data therefore strongly implicates the presence of iron within the lumen of the gastrointestinal tract as being the colorectal cancer causing agent rather than the systemic circulating pool of iron. Furthermore, other studies have shown that colonic neoplasms have a higher iron content that normal mucosa.

It is known that the amount of iron consumed in a typical diet exceeds the amount of iron actually absorbed by the body. In normal individuals only approximately 10% of dietary iron is absorbed. Iron is absorbed by the small intestine, and excess iron that is not absorbed passes through the colon. However, a reduction in dietary iron is not a suitable treatment for patients with colorectal cancer, as a reduction in dietary iron will reduce not only the amount of iron in the colon, but also the amount of iron which is absorbed into the blood. As a result, the patient will become iron deficient and ultimately anaemic. Furthermore, it is unknown at present what effect low circulating iron might have on carcinogenesis. The present invention therefore overcomes this problem by providing a composition which reduces the amount of iron in the colon, without affecting systemic iron levels.

To reduce iron levels in the colon, the composition comprises a chelator—a chemical which binds iron. Alginates are an example of a naturally-occurring chelator of iron and are used by the UK food industry as gelling, emulsifying and stabilising agents and thus are extensively found in products such as ice creams, jams, sauces and desserts. Alginates are also found in medicines, particularly in anti-reflux medicines. Alginates are therefore known to be safe for consumption by humans and animals. A further advantage of alginates is that they cannot be digested or absorbed by the human body. Both in vitro and in vivo studies have shown that alginates can stably bind iron and may prevent iron absorption. In particular, studies carried out by the inventors have shown that iron-mediated cellular proliferation is inhibited in the presence of alginate (unpublished data), and that alginates may have a beneficial effect on the colonic microbiota.

EXAMPLE ORAL FORMULATIONS

| A. Iron Chelators | B. Delivery Component |
|---|---|
| 1. Phytic acid | a. pH-sensitive (e.g Eudragit FS30D) |
| 2. Polyphenols | b. Time-dependent (e.g. the Pulsincap ™ and Chronotopic systems) |
| 3. Alginates | c. Pressure-dependent (e.g. pressure-controlled colon-delivery capsules have been formulated utilising ethylcellulose) |
| | d. Biodegradable (e.g. pectin, guar gum and chitosan) |
| | f. Microsponges (e.g. microsponge ® 5640) |
| | g. Osmotic pump (e.g. the microbially-triggered colon-targeted osmotic pump) |

A composition comprising an iron chelator selected from list A is coated with a colonic-delivery component selected from list B to give compositions 1a to 1g, 2a to 2 g and 3a to 3g.

Example 1

A composition comprising microcrystalline cellulose, sugar, propyl paraben and 0.5 g sodium alginate is formulated into a 1 g tablet and coated with a biodegradable polysaccharide. Two tablets are orally administered to a patient with colorectal cancer three times a day at 4 hourly intervals.

The invention claimed is:

1. A method of treating a mammal afflicted with colorectal cancer, the method comprising the oral administration to a mammal in need of a therapeutically effective amount of a biologically acceptable composition comprising an iron chelator, wherein the composition is encapsulated or microencapsulated by a coating which remains intact while the composition passes through the stomach and small intestine, but which degrades in the colon, such that the iron chelator is prevented from binding iron until it reaches the colon, and wherein the iron chelator is non-digestible, non-absorbable and non-fermentable in the gastrointestinal tract.

2. A method according to claim 1, wherein the iron chelator is alginate.

3. A method according to claim 2, wherein the amount of alginate administered is no more than 15 g per day.

* * * * *